United States Patent
Kuntz et al.

(10) Patent No.: US 11,771,482 B2
(45) Date of Patent: Oct. 3, 2023

(54) IMPLANTS FOR TISSUE FIXATION AND FUSION

(71) Applicant: CUTTING EDGE SPINE LLC, Mineral Springs, NC (US)

(72) Inventors: Kyle Kuntz, Waxhaw, NC (US); Shyam Patel, Waxhaw, NC (US)

(73) Assignee: CUTTING EDGE SPINE LLC, Mineral Springs, NC (US)

( * ) Notice: Subject to any disclaimer, the term of this patent is extended or adjusted under 35 U.S.C. 154(b) by 103 days.

(21) Appl. No.: 17/183,330

(22) Filed: Feb. 23, 2021

(65) Prior Publication Data

US 2021/0196333 A1 Jul. 1, 2021

Related U.S. Application Data

(63) Continuation of application No. 15/976,989, filed on May 11, 2018, now Pat. No. 10,993,754.

(Continued)

(51) Int. Cl.
*A61B 17/86* (2006.01)
*A61B 17/70* (2006.01)
(Continued)

(52) U.S. Cl.
CPC ............ *A61B 17/869* (2013.01); *A61B 17/70* (2013.01); *A61B 17/7055* (2013.01);
(Continued)

(58) Field of Classification Search
CPC ... A61B 17/869; A61B 17/70; A61B 17/7055; A61B 17/764; A61B 2017/00526;
(Continued)

(56) References Cited

U.S. PATENT DOCUMENTS 5,282,861 A * 2/1994 Kaplan .................. B22F 3/114
623/23.51
5,417,692 A 5/1995 Goble et al.
(Continued)

FOREIGN PATENT DOCUMENTS

RU 2150964 C1 6/2000
RU 2172146 C1 8/2001
(Continued)

OTHER PUBLICATIONS

Zimmer Trabecular Metal Dental Implant Brochure; trabecular metal.zimmerdental.com, 2012, Carlsbad, California.
(Continued)

*Primary Examiner* — Jessica Weiss
(74) *Attorney, Agent, or Firm* — McNees Wallace & Nurick LLC (57) ABSTRACT

A fixation implant includes a head, a shank and a distal tip, and one or more of the head, shank and distal tip may be cannulated. The shank includes a threaded ingrowth portion extending from the head to the tapered distal tip that includes external threads, and at least one open network body extending along the length of the ingrowth portion. The open network body selected from one or a combination of a helix, an arrangement of trusses, a scaffold of open and interconnected pores, a porous framework of random open and interconnected pores, and combinations of these.

17 Claims, 10 Drawing Sheets

Related U.S. Application Data (60) Provisional application No. 62/505,257, filed on May 12, 2017.

(51) Int. Cl.
    *A61F 2/44*         (2006.01)
    *A61F 2/30*         (2006.01)
    *A61B 17/00*       (2006.01)

(52) U.S. Cl.
    CPC .......... *A61B 17/864* (2013.01); *A61F 2/4455* (2013.01); *A61B 2017/00526* (2013.01); *A61F 2002/3085* (2013.01); *A61F 2002/3092* (2013.01); *A61F 2002/30593* (2013.01); *A61F 2002/30622* (2013.01); *A61F 2002/30985* (2013.01); *A61F 2002/30995* (2013.01)

(58) Field of Classification Search
    CPC .......... A61B 2017/30593; A61B 2017/30622; A61B 2017/3085; A61B 2017/3092; A61B 2017/30985; A61B 2017/30995; F16B 25/00; F16B 25/0036; F16B 25/0078; F16B 25/0094
    USPC .................... 606/300–321; 411/411, 424
    See application file for complete search history.

(56) References Cited

U.S. PATENT DOCUMENTS

| | | | |
|---|---|---|---|
| 6,375,655 B1 | 4/2002 | Zdeblick et al. | |
| 6,960,216 B2 | 11/2005 | Kolb et al. | |
| 7,458,991 B2 | 12/2008 | Wang et al. | |
| 7,534,254 B1 | 5/2009 | Michelson | |
| 7,736,381 B2 | 6/2010 | Biedermann et al. | |
| 8,057,475 B2 | 11/2011 | Michelson | |
| 8,075,312 B2 | 12/2011 | Collins et al. | |
| 8,137,389 B2 | 3/2012 | Biedermann et al. | |
| 8,231,387 B2 | 7/2012 | Salvi et al. | |
| 8,414,654 B1 | 4/2013 | Ganey | |
| 8,430,930 B2 | 4/2013 | Hunt | |
| 8,864,839 B2 | 10/2014 | Ganey | |
| 8,899,982 B2 | 12/2014 | Damstra et al. | |
| 8,900,279 B2 | 12/2014 | Assell et al. | |
| 8,968,372 B2 | 3/2015 | Biedermann et al. | |
| 8,979,911 B2 | 3/2015 | Martineau et al. | |
| 9,095,396 B2 | 8/2015 | Collins et al. | |
| 9,179,954 B2 | 11/2015 | Ganey | |
| 9,421,108 B2 | 8/2016 | Hunt | |
| 9,468,483 B2 | 10/2016 | Biedermann et al. | |
| 9,545,317 B2 | 1/2017 | Hunt | |
| 9,636,226 B2 | 5/2017 | Hunt | |
| 9,662,157 B2 | 5/2017 | Schneider et al. | |
| 9,724,203 B2 | 8/2017 | Nebosky et al. | |
| 9,949,834 B2 | 4/2018 | Pressacco | |
| 9,987,065 B2 | 6/2018 | De Lavigne Sainte Suzanne | |
| 9,999,516 B2 | 6/2018 | Hunt | |
| 10,194,962 B2 | 2/2019 | Schneider et al. | |
| 10,285,816 B2 | 5/2019 | Roby et al. | |
| 10,321,940 B2 | 6/2019 | Anderson et al. | |
| 2006/0111715 A1* | 5/2006 | Jackson ................ | A61B 17/86 606/61 |
| 2006/0116679 A1 | 6/2006 | Lutz et al. | |
| 2006/0276788 A1 | 12/2006 | Berry et al. | |
| 2007/0055244 A1* | 3/2007 | Jackson ................ | A61B 17/864 606/86 A |
| 2007/0065779 A1 | 3/2007 | Mangano | |
| 2007/0162019 A1 | 7/2007 | Burns et al. | |
| 2009/0254126 A1 | 10/2009 | Orbay et al. | |
| 2009/0259261 A1 | 10/2009 | Reiley | |
| 2010/0042167 A1* | 2/2010 | Nebosky ............... | A61M 37/00 606/301 |
| 2010/0094292 A1 | 4/2010 | Parrott | |
| 2010/0094420 A1 | 4/2010 | Grohowski, Jr. | |
| 2010/0137990 A1 | 6/2010 | Apatsidis et al. | |
| 2010/0145393 A1 | 6/2010 | Fallin et al. | |
| 2011/0060373 A1* | 3/2011 | Russell ............... | A61B 17/8875 606/86 R |
| 2012/0265256 A1 | 10/2012 | Biedermann et al. | |
| 2012/0271362 A1* | 10/2012 | Martineau ............... | B22F 7/008 470/9 |
| 2013/0072933 A1 | 3/2013 | Biedermann et al. | |
| 2013/0123935 A1 | 5/2013 | Hunt et al. | |
| 2013/0178900 A1 | 7/2013 | Fallin et al. | |
| 2013/0245763 A1 | 9/2013 | Mauldin | |
| 2014/0039565 A1* | 2/2014 | Martineau ............ | A61B 17/864 606/304 |
| 2014/0046379 A1* | 2/2014 | Sweeney ............... | A61B 17/863 606/304 |
| 2014/0277461 A1* | 9/2014 | Nebosky ................ | A61F 2/442 156/60 |
| 2015/0127057 A1* | 5/2015 | Ganey ................. | A61F 2/30767 606/309 |
| 2015/0209094 A1* | 7/2015 | Anderson .............. | B33Y 80/00 470/10 |
| 2015/0282946 A1 | 10/2015 | Hunt | |
| 2015/0313658 A1 | 11/2015 | Kolb | |
| 2016/0157908 A1 | 6/2016 | Cawley et al. | |
| 2016/0166301 A1 | 6/2016 | Papangelou et al. | |
| 2017/0095337 A1 | 4/2017 | Pasini et al. | |
| 2017/0216035 A1 | 8/2017 | Hunt | |
| 2018/0085230 A1 | 3/2018 | Hunt | |
| 2018/0214192 A1 | 8/2018 | Roby et al. | |
| 2019/0159818 A1 | 5/2019 | Schneider et al. | |
| 2019/0239935 A1 | 8/2019 | Willis et al. | |

FOREIGN PATENT DOCUMENTS

| | | | |
|---|---|---|---|
| WO | 2001005325 | 8/2001 | |
| WO | 2002034120 A2 | 5/2002 | |
| WO | 2002038054 | 5/2002 | |
| WO | 2006127392 A2 | 11/2006 | |
| WO | 2008021474 A2 | 2/2008 | |
| WO | 2008044011 A2 | 4/2008 | |
| WO | 2008101932 A2 | 8/2008 | |
| WO | 2010002663 A1 | 1/2010 | |
| WO | 2010045116 A1 | 4/2010 | |
| WO | 2010080511 A1 | 7/2010 | |
| WO | 2011044697 A1 | 4/2011 | |
| WO | 2011086529 A1 | 7/2011 | |
| WO | 2012171011 A1 | 12/2012 | |
| WO | 2013006778 A2 | 1/2013 | |
| WO | 2013067528 A1 | 5/2013 | |
| WO | 2013077897 A1 | 5/2013 | |
| WO | 2013091392 A1 | 6/2013 | |
| WO | WO-2013091392 * | 6/2013 | ............ A61B 17/86 |
| WO | 2013134678 A1 | 9/2013 | |
| WO | 2013150369 A1 | 10/2013 | |
| WO | 2014068259 A1 | 5/2014 | |
| WO | 2014143719 A1 | 9/2014 | |
| WO | 2014145529 A1 | 9/2014 | |
| WO | 2015164982 A1 | 11/2015 | |
| WO | 2016099620 A1 | 6/2016 | |
| WO | 2017096199 A1 | 6/2017 | |
| WO | WO-2017201371 A1 * | 11/2017 | ............... A61F 2/28 |
| WO | 2018100250 A1 | 6/2018 | |
| WO | 2018140375 A1 | 8/2018 | |
| WO | 2018215756 A1 | 11/2018 | |
| WO | 2019050392 A1 | 3/2019 | |
| WO | 2019122473 A1 | 6/2019 | |
| WO | 2019126199 A1 | 6/2019 | |

OTHER PUBLICATIONS

PCT Notification of Transmittal of the International Search Report and the Written Opinion of the ISR issued for PCT/US2018/032215 dated Sep. 6, 2018.

* cited by examiner

IMPLANTS FOR TISSUE FIXATION AND FUSION

RELATED APPLICATION

This application is a continuation of U.S. Nonprovisional application Ser. No. 15/976,989 filed on May 11, 2018, which claims the benefit under 35 U.S.C. § 119(e) to U.S. Provisional Application Ser. No. 62/505,257 filed May 12, 2017, the entirety of which is incorporated herein by reference.

FIELD

The present application describes various exemplary devices and surgical techniques for securing tissue, particularly bone tissue, and more particularly in some examples, bone tissue in the spine associated with the sacroiliac joint.

DESCRIPTION OF THE RELATED ART

In the context of orthopedics, a variety of conditions, including injuries, degeneration, and congenital abnormalities can present the need for interventional implants and surgical techniques to achieve one or more of bone repair, stabilization, and correction. Conventional procedures have been developed using mechanical implants, for example to straighten or otherwise stabilize joints, secure fragments of fractured bones, and secure and stabilize successive vertebrae, sacral iliac bones, and other adjacent bones in a fixed position. These implants include bone screws, anchors, rods, bands, plates, and combinations of these devices that are comprised of one or a combination of metal, polymers, biomaterials and other biologically acceptable materials.

In one example, fixation and fusion is needed for addressing sacroiliac dysfunction or instability that occurs in the sacroiliac joint. In a typical subject, the sacroiliac joint spans between the sacrum bone and ilium bone, and has a natural degree or motion, or nutation, of one to two degrees. In the case of injury to the joint, the typically small range of motion can be exaggerated and lead to hypermobility, an often difficult condition to diagnose because it involves lower back and leg pain which are symptoms that are common with other spinal and orthopedic problems. Once diagnosed, there are surgical options for fixation and fusion of the sacroiliac joint. But due to the natural movement of the joint, typical bone screw type implants can be vulnerable to rotation and ultimate failure.

Accordingly, there is a need for implant devices that can straighten or otherwise stabilize joints, secure fragments of fractured bones, and secure and stabilize successive vertebrae, sacral iliac bones, and other adjacent bones in a fixed position. Such improved devices are needed for the maintenance of stability of securement of the bones, for example prevention of rotation of one or both of bone and implant that can destabilize fixation and cause movement or migration of the joined bone, of the implant, and combinations of these. Thus, applications would include correcting instability and hypermobility in fixated joints, and providing resistance to rotational and pull out failures in order to achieve the desirable degree of fusion across a joint, across joined portions of bone, and in the context of implants secured to bone. In some particular applications, there is a need for devices that enhance and provide more secure fixations of the sacroiliac joint, including greater bone purchase and retention, and features for enhanced tissue integration.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 9B shows three alternate embodiments of a fixation implant, the uppermost image depicting an cannulated implant having a solid-walled inner cylindrical through channel, the implant having exterior threading and an interior framework of random open and interconnected pores, shown in a side cross sectional view; the middle image depicting an cannulated implant having a solid-walled inner cylindrical through channel, the implant having a cylindrical head, exterior threading from the head to the distal tip and an interior framework of random open and interconnected pores, shown in a side cross sectional view; and, the third and bottom image depicting an cannulated implant having a solid-walled inner cylindrical through channel, the implant having a cylindrical head, exterior threading at the head and on a portion of the shank and at the distal tip and an interior framework of random open and interconnected pores, shown in a side cross sectional view.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community, and generally, any and all terms providing spatial references to anatomical features shall have meaning that is customary in the art. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced.

"Patient" is used to describe an animal, preferably a human, to whom treatment is administered, including prophylactic treatment with the compositions of the present invention. "Concave" is used herein to describe an indented surface without reference to the specific shape of the indented surface. As non-limiting examples, the concave face may be tubular with a round cross section, oval cross section, square cross section, or rectangular cross section.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, some references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

The present application describes various embodiments of devices for joint and other bone fixation. In some particular embodiments, devices for fixation of the sacroiliac joint are provided. It will be appreciated that the examples and drawings, as shown herein, may be described in reference to use in applications for sacroiliac joint fusion, though the devices as disclosed herein may be used in any of a variety of other orthopedic applications, and may be used alone, or as an adjunct to devices used for other fixation or correction, such as, for example, in spine fusion surgery, to help hold other implants in place.

Fixation Implants

In accordance with various embodiments, the invention provides a fixation implant that comprises fixation member having a proximal head and a shank with a distal tip. The fixation implant is advantageously used for accomplishing fixation of tissue, such as bone tissue, in some examples including adjacent bones at a joint such as the sacroiliac joint, or bone fracture fragments. The implant provides enhanced resistance to rotational motion, rotational migration and pull out as compared with other fixation member designs, this advantage owing to one or more of increased bone engagement surface, enhanced opportunity for osseointegration, and enhanced bone purchase as a result of the extensively enhanced surface area of the three-dimensional open structure of at least a portion of the implant. The fixation implant includes one or more of head and shank features modeled to resemble the open and interconnected porosity features of trabecular bone in a variety of different embodiments.

In accordance with the various embodiments, the shank of the fixation member includes one or more openings or slots through the shank, in some embodiments arranged as a plurality around the periphery of the shank, to further enhance bony ingrowth. The openings are referred to herein as an open core and are formed of an open network body that provides a framework comparable to that of trabecular bone. As further described herein, an open core may be formed within any of the head and the shank portions and comprises at least one open network body. In some particular embodiments, the shank portion includes an open core comprising an open network body and one or both of the head and distal tip are solid (i.e., do not include an open network body) and may include a through cannula. In some embodiments, an open network body may be selected from one or a combination of: at least one elongate helix; an organized arrangement of trusses; a random arrangement of trusses; a framework or scaffold of random open and interconnected pores; and, a porous framework of random open and interconnected pores. Thus, in some embodiments, the entire fixation implant may have an open core formed of at least one type of open network structure or combinations thereof.

In accordance with the various embodiments, the open network body of the fixation implant allows materials to move into or out of the open core of the shank, the materials including bone fillers and other materials that would encourage bony ingrowth. Of course, in some such embodiments, the fixation implants may be provided without any filler materials. In accordance with the various embodiments, all or any portion of the fixation implant may be formed of one or more of a metal and a polymer. In particular, the head, the shank, the open core and the distal tip may be partially or completely formed from one or a combination of materials selected from metal and a polymer. In some particular examples, all or a portion of the materials forming the trabecular body may be osseo-inductive, selected from materials such as titanium, or others. And in some embodiments, the entire fixation implant may have an open core formed of a metal, a polymer, or combinations of these with or without other additive materials such as hydroxyapatite, and the open core may be open or closed.

Figure 1:
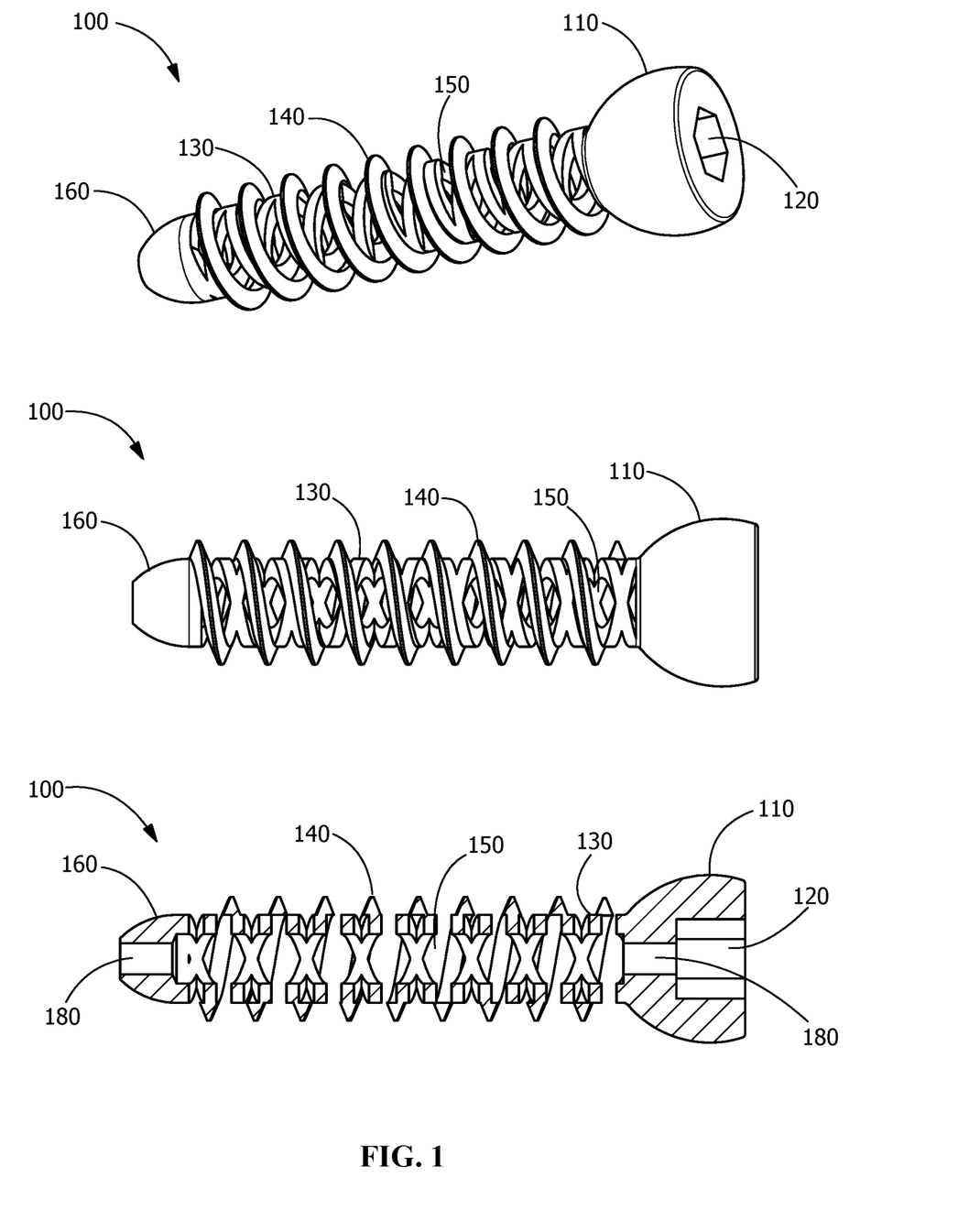
FIG. 1 shows another embodiment of a fixation implant characterized in having an external thread over an open helical body, and shown in oblique, side and side cross sectional views.

An open network body has an open and interconnected matrix that allows communication between all bony material 360 degrees around the bone to optimize complete bony integration. This is advantageous over existing screw designs that have one or a series of fenestrations in an otherwise solid body of the shank, such fenestrations providing incomplete (i.e., less than 360 degree) engagement with bone. The three-dimensional structures of the open network body can provide greater support and stress distribution as compared to through holes and other fenestrations in the body of the shank of a conventional hollow screw that is designed to encourage bony ingrowth. Similar to the function of the trabeculae in bone, the open network structures of the open network body can allow for more even stress distribution than fenestrations would permit while also presenting open portions for bony ingrowth circumferentially at all points of circumferential contact with bone Referring now to FIG. 1, an exemplary embodiment of a fixation member 100 is shown. The fixation member 100 is characterized in having a head 110, and a shank 130 with an external thread 140 over an open core comprising a helical body 150 having the shape of a helix along the length of the shank 130, the fixation member 100 generally resembling the overall shape of a bone screw. According to the various embodiments, the open core as shown in FIG. 1 in the form of a helical body 150 provides an example of an open network body according to the invention that is adapted to encourage bony growth through the implant when it is fixed in bone. As shown in FIG. 1 and the other embodiments, the thread 140 is disposed on and integral with the helical body 150 forming the open network body of the open core, such that the helical body 150 is at least partially visible along the length of at least a portion of the shank 130 in the gaps between the thread 140, providing access into the helical body 150 to allow tissue infiltration and bony ingrowth therein.

Figure 7:
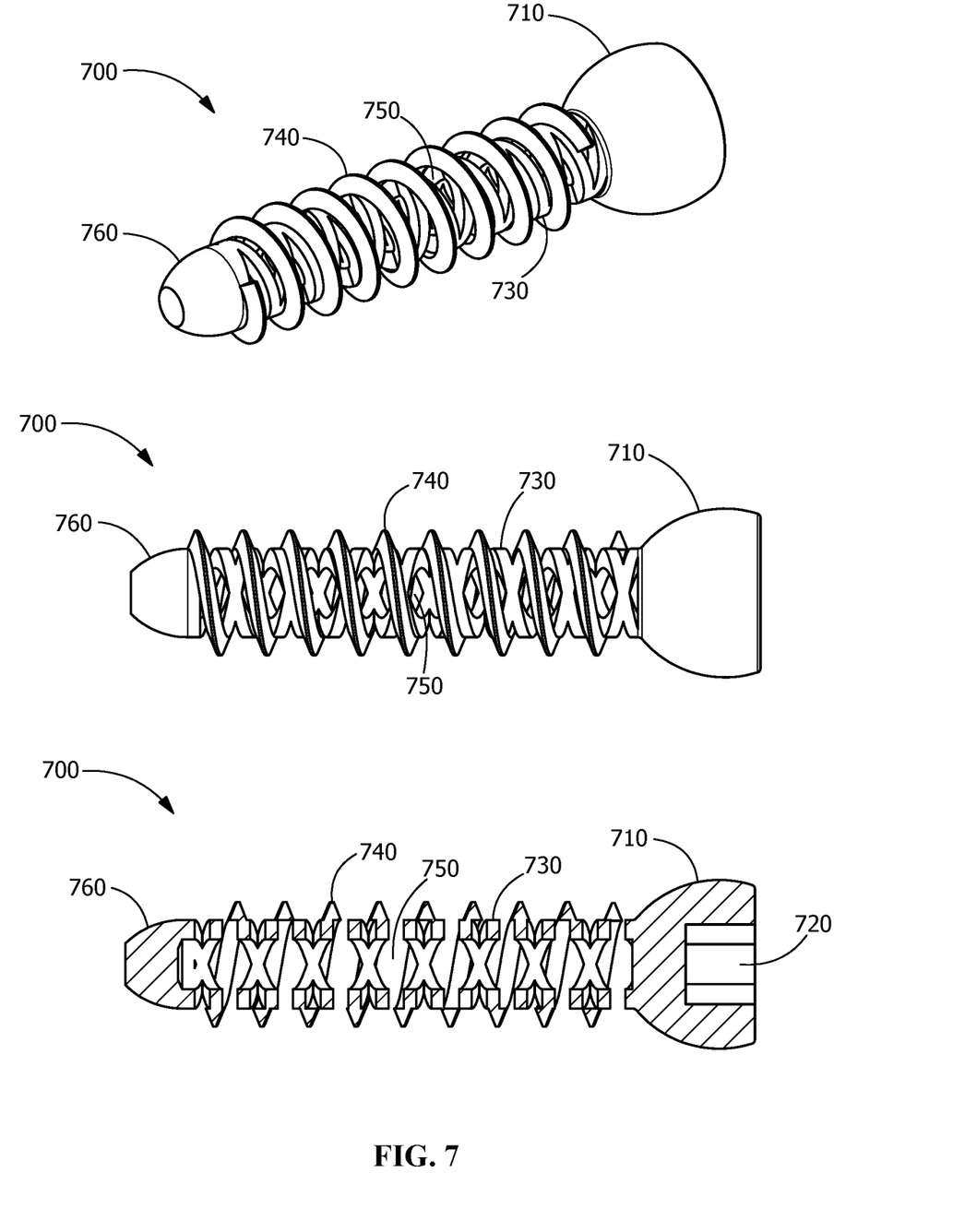
FIG. 7 shows another embodiment of a fixation implant characterized in having an external thread over an open helical body, wherein the implant is not cannulated and is shown in oblique, side and side cross sectional views.

Referring again to FIG. 1, in the exemplified embodiment, the fixation implant 100 includes a proximal head 110 that has a generally spherical in shape, and comprises a center through cannula 180 that passes from the head 110 through the distal tip 160, and a tool recess 120 for engaging a driving instrument. In alternate embodiments the head shape may be generally hemispherical, generally cylindrical, generally conical, and generally frustoconical. Each of the head 110 and distal tip 160 is cannulated and otherwise solid (i.e., it is not formed of an open network). In alternate embodiments, one or more of the distal tip 160 and the head 110 may be non-cannulated and solid, or may be cannulated and partially or entirely formed from one of a solid and an open network. Referring now to FIG. 7-FIGS. 9A and B, as shown in alternate depicted embodiments, for example as shown in FIG. 7, the head 710 and distal tip 760 are solid (not cannulated).

The exemplified fixation implant 100 includes a shank 130 having a length defined between the proximal head 110 and a distal tip 160 and a shape that is generally cylindrical that does not taper from proximal to distal, with a distal tip 160 that is a tapered frustoconical shape. In alternate various embodiments, the shank shape is selected from generally cylindrical, generally conical and generally frustoconical. It will be appreciated that the shape and proportions of the implant are not intended to be limiting and that the relative dimensions of each of the head, shank and distal tip portions of the various embodiments may vary. In the various alternate embodiments, all or only a portion of the shank 130 may have one or more an external thread 140 arranged around the open core along the length of the shank 130.

In the various embodiments according to the disclosure, the open core is formed with an open network structure selected from one or a combination of: at least one elongate helix; an organized arrangement of trusses; a random arrangement of trusses; a framework or scaffold of random open and interconnected pores; and, a porous framework of random open and interconnected pores. Further, the open core may be open in its center (whether or not one or both of the head and the distal tip are cannulated), or it may be solid, or it may include an open network structure as described herein above, or it may comprise a solid inner wall, such as a cylindrical wall, or a fenestrated wall, or a combination of these. As briefly described herein, each of FIG. 1, FIG. 3, FIG. 5, FIG. 6 and FIG. 7 depicts a fixation implant in which the open core has an open center (where FIG. 7 is the one example in which the head and the distal tip are not cannulated), and, each of FIG. 2 and FIG. 4 depicts a fixation implant in which the open core includes at its center a solid cylindrical wall that is cannulated, and FIG. 8 and FIGS. 9A and B each depict fixation implants in which the open core has a center that is continuously filled with the open network, and in which the head and the distal tip are not cannulated.

It will be appreciated by one of ordinary skill in the art that while each of the depicted embodiments as shown in the drawings include various combinations of the features that include a head and a distal tip and a shank comprising one or open network bodies, there are numerous possible embodiments having combinations of features that are not shown in the drawings. Thus, in various alternate examples, the fixation implant may have any one or more of the following configurations along at least a portion of its length between the head and the distal tip, from proximal to distal: a through cannula surrounded by an open network body with exterior threading; a through cannula surrounded by a solid or fenestrated wall that is surrounded by an open network body with exterior threading; a solid that is surrounded by an open network body with exterior threading; and, a continuous open network body with exterior threading. Thus, FIG. 1 is an example of a fixation implant that has a through cannula from the proximal head portion through the distal tip, each of the proximal head portion and tip being otherwise solid (not an open network) and the shank comprises a void (the through cannula) surrounded by an open network body.

Figure 2:
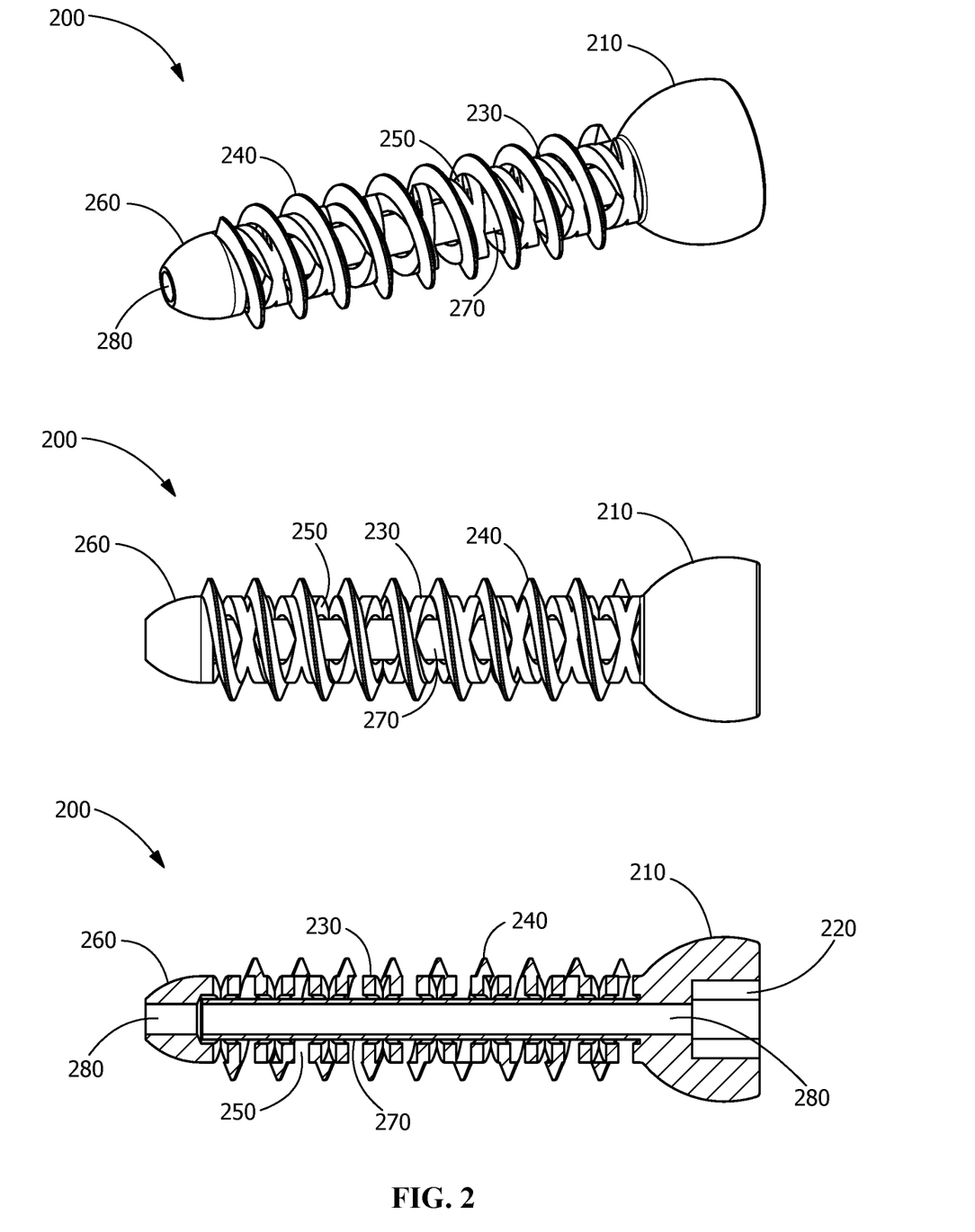
FIG. 2 shows yet another embodiment of a fixation implant characterized in having an external thread over an open helical body having an solid-walled inner cylindrical through channel, and shown in oblique, side and side cross sectional views.

Referring now to FIG. 2, yet another embodiment of a fixation implant 200 is shown being characterized in having a shank 230 comprising an external thread 240 over an open core, the open core comprising a helical body 250 having the shape of a helix along the length of the shank 230, the helical body 250 having within it a solid-walled inner cylindrical through channel 270. In the depicted embodiment, each of the head 210 and the distal tip 260 are cannulated 280, and the head 210 includes a tool recess 220 for engaging a driving instrument.

Figure 3:
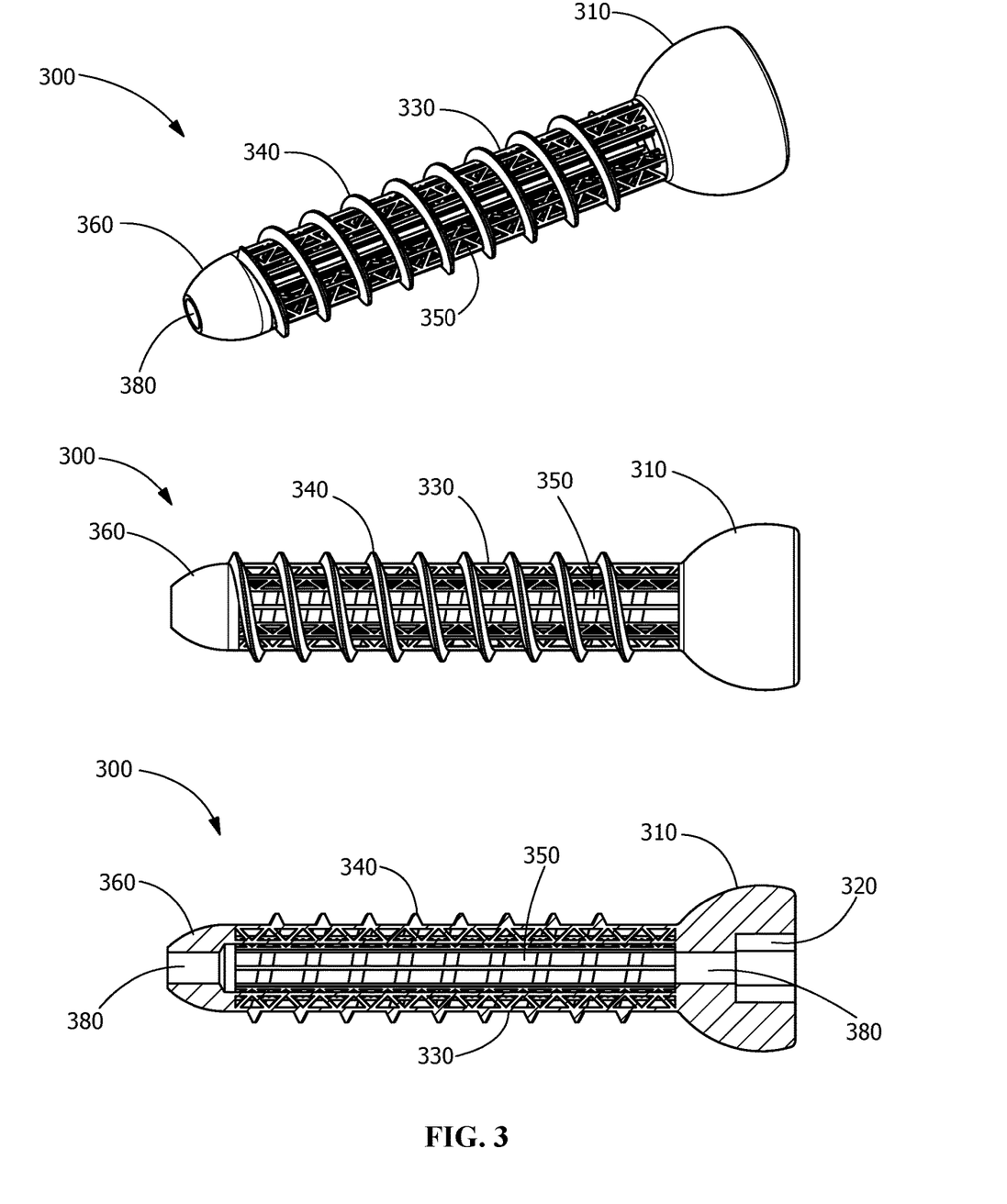
FIG. 3 shows yet another embodiment of a fixation implant characterized in having an external thread over an open organized truss arrangement, and shown in oblique, side and side cross sectional views.
Figure 4:
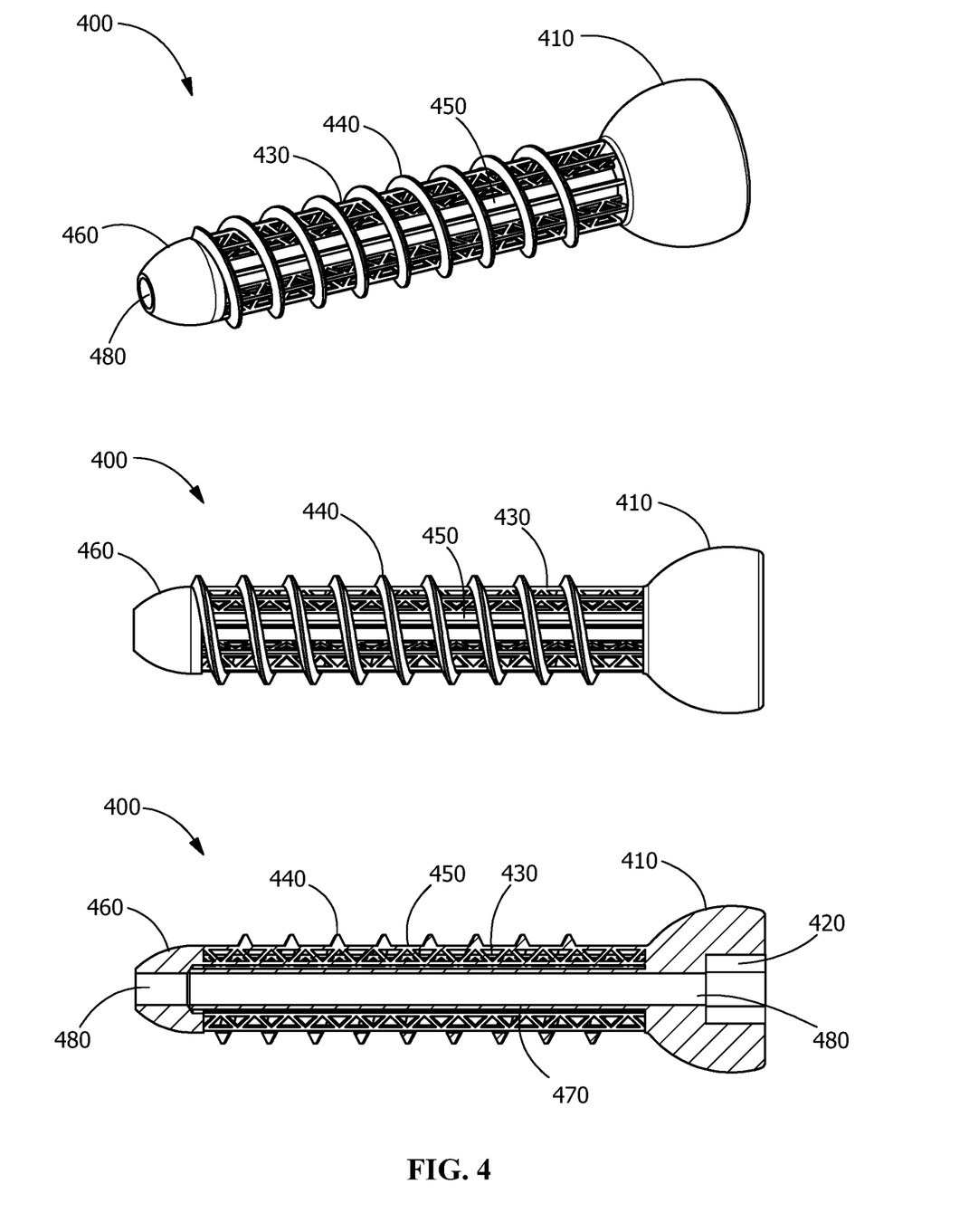
FIG. 4 shows another embodiment of a fixation implant characterized in having an external thread over an open organized truss arrangement with a solid-walled inner cylindrical through channel, and shown in oblique, side and side cross sectional views.

Referring now to FIG. 3, yet another embodiment of a fixation implant 300 is shown being characterized in having a shank 330 comprising an external thread 340 over an open core, the open core comprising an organized truss body 350. In the depicted embodiment, each of the head 310 and the distal tip 360 are cannulated 380, and the head 310 includes a tool recess 320 for engaging a driving instrument.

Referring now to FIG. 4, yet another embodiment of a fixation implant is shown having a shank 430 comprising an external thread 440 over an open core, the open core comprising an organized truss body 450 that has a solid-walled inner cylindrical through channel 470. In the depicted embodiment, each of the head 410 and the distal tip 460 are cannulated 480, and the head 410 includes a tool recess 420 for engaging a driving instrument.

Figure 5:
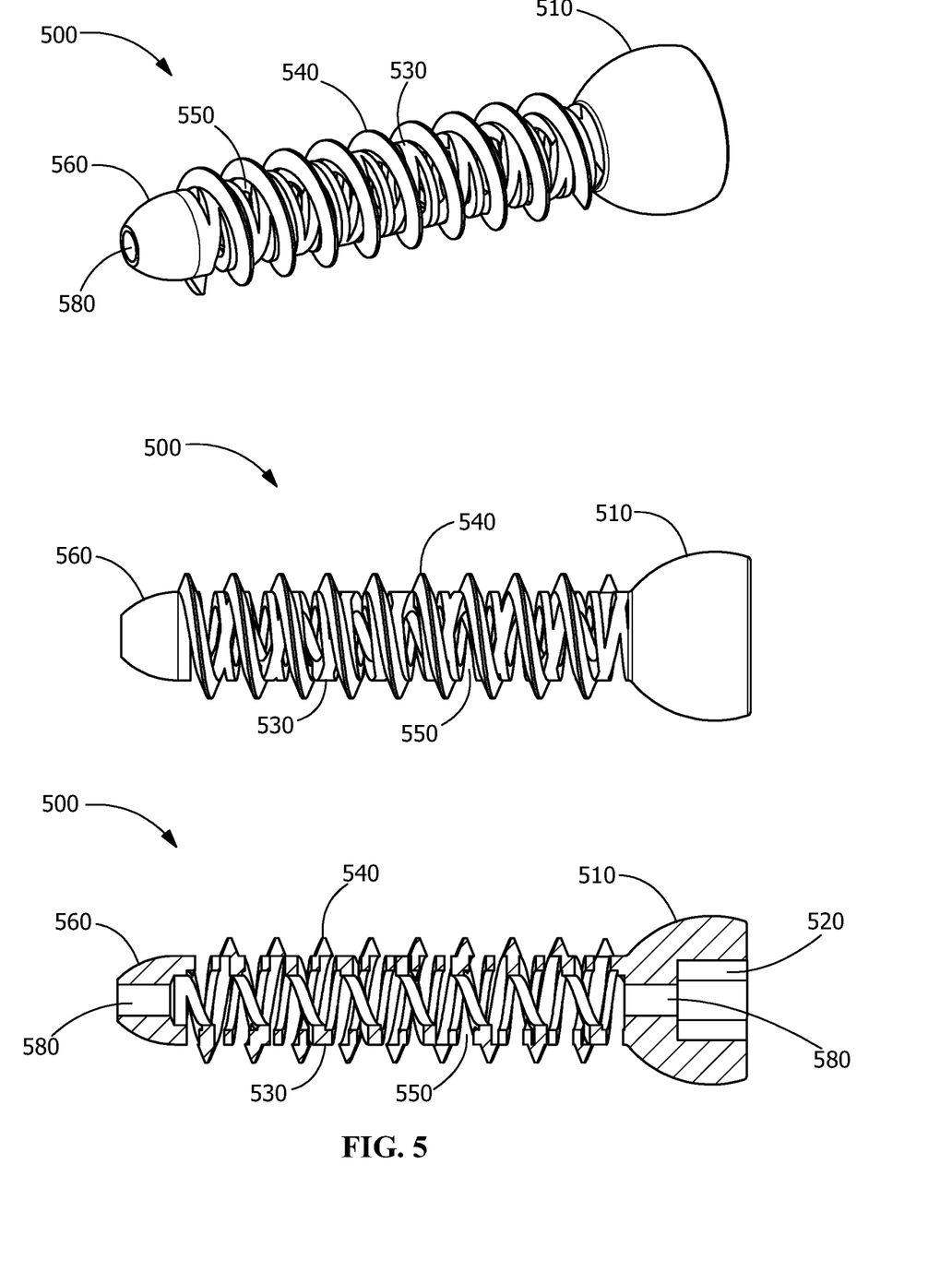
FIG. 5 shows another embodiment of a fixation implant characterized in having an external thread over an open helical body that includes two helices having different pitches, and shown in oblique, side and side cross sectional views.

FIG. 5 shows yet another embodiment of a fixation implant 500, the fixation implant 500 having a shank 530 characterized in having an external thread 540 over an open core comprising a dual helical body 550 that comprises two entwined helices, each helix having a different pitch. In the depicted embodiment, each of the head 510 and the distal tip 560 are cannulated 580, and the head 510 includes a tool recess 520 for engaging a driving instrument.

Figure 6:
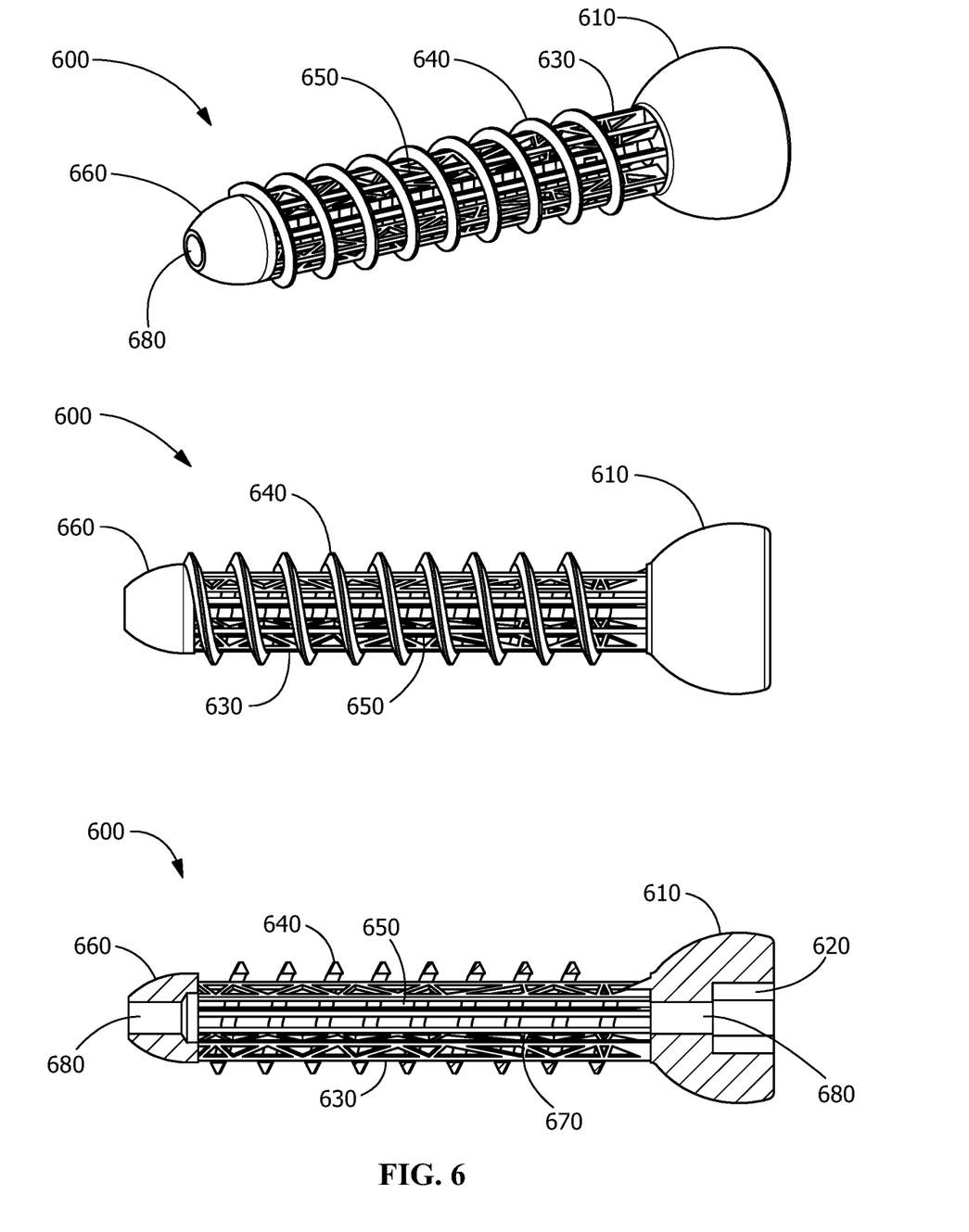
FIG. 6 shows another embodiment of a fixation implant characterized in having an external thread over an open disorganized truss arrangement with a fenestrated solid-walled inner cylindrical through channel, and shown in oblique, side and side cross sectional views.

Referring now to FIG. 6, yet another embodiment of a fixation implant 600 is shown being characterized in having a shank 630 having an external thread 640 over an open core comprising a disorganized truss body 650 with a solid-walled inner cylindrical through channel 670 that is fenestrated along its length and open to the threading as shown in the lower panel of FIG. 6. In the depicted embodiment, each of the head 610 and the distal tip 660 are cannulated 680, and the head 610 includes a tool recess 620 for engaging a driving instrument.

Referring now to FIG. 7, yet another embodiment of a fixation implant 700 is shown being characterized in having a shank 730 having an external thread 740 over an open (containing a void) helical body 750, where in the depicted embodiment, each of the head 710 and the distal tip 760 are not cannulated, and the head 710 includes a tool recess 720 for engaging a driving instrument.

Figure 8:
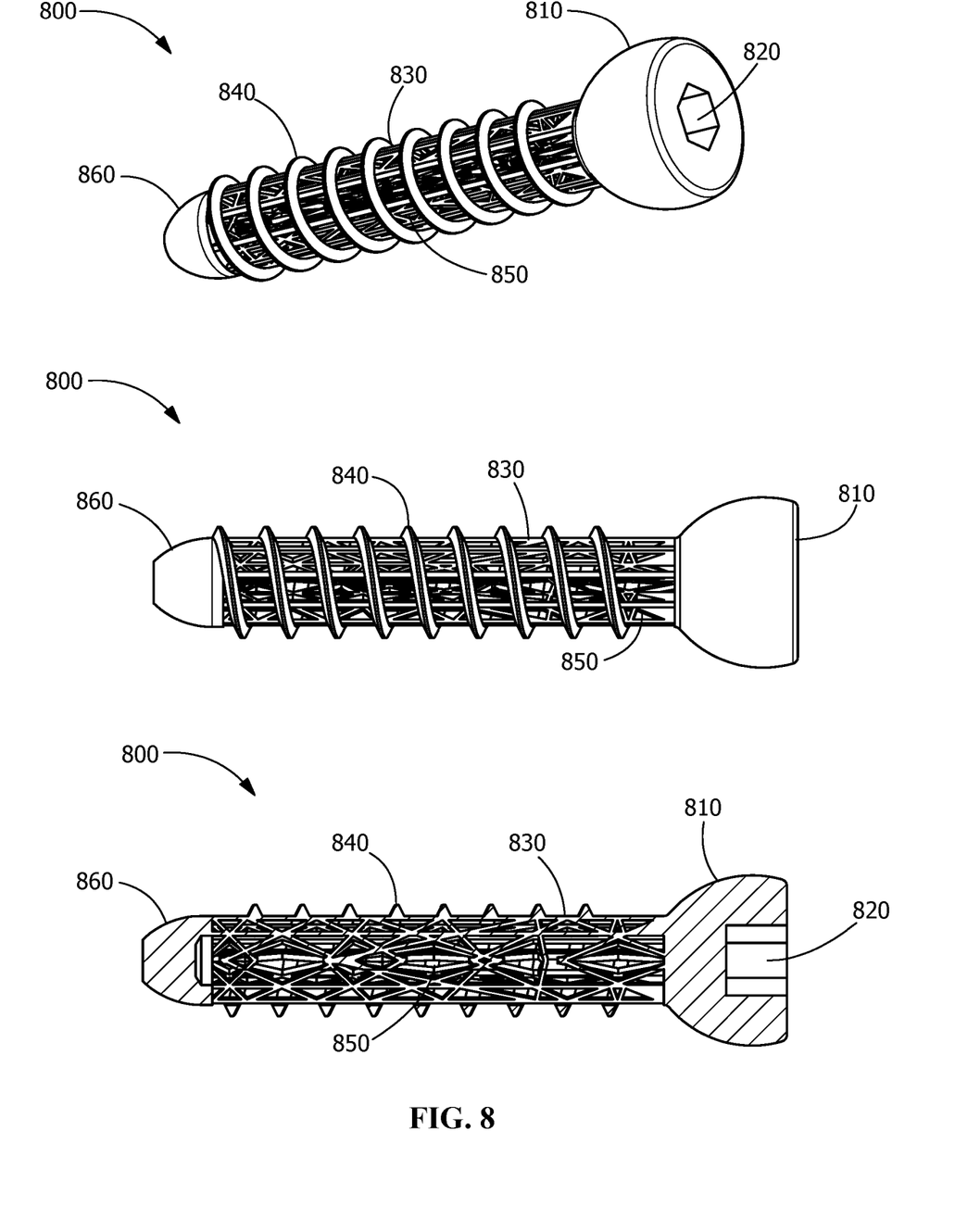
FIG. 8 shows another embodiment of a fixation implant characterized in having an external thread over an open and continuous disorganized truss arrangement wherein the implant is not cannulated and is shown in oblique, side and side cross sectional views.

Referring now to FIG. 8, yet another embodiment of a fixation implant 800 is shown being characterized in having a shank 830 having an external thread 840 over an open and continuous disorganized truss body 850 wherein the shank 830, the head 810 and the distal tip 860 are not cannulated, and the head 810 includes a tool recess 820 for engaging a driving instrument.

Figure 9A:
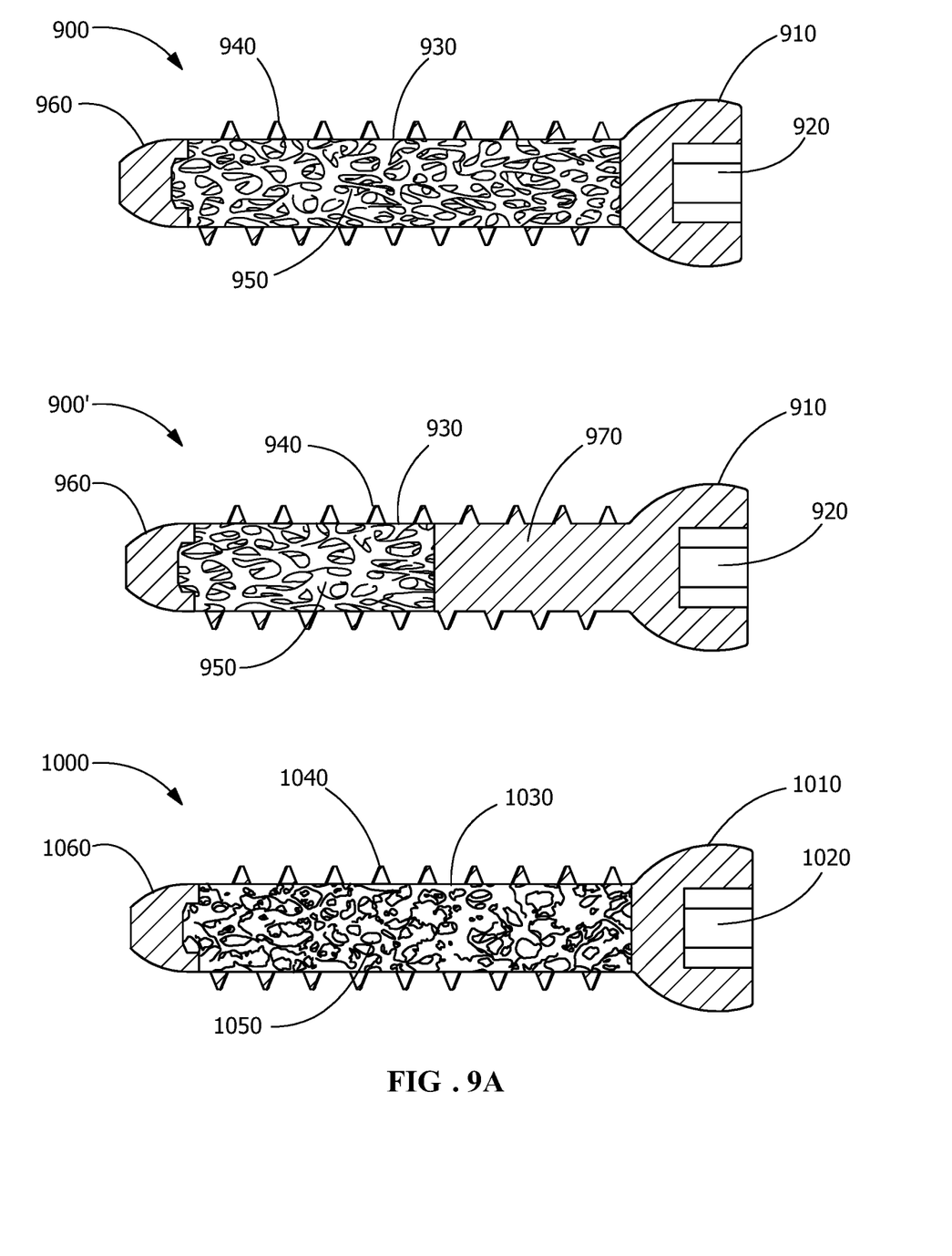
FIG. 9A shows three alternate embodiments of a fixation implant, the uppermost image depicting an non-cannulated implant having exterior threading and an interior framework of random open and interconnected pores, shown in a side cross sectional view; the middle image depicting a variation of the fixation member of the upper image that is only partially formed with the interior framework, shown in a side cross sectional view; and, the third and bottom image depicting an alternate embodiment of an non-cannulated implant having exterior threading and a porous interior framework of random open and interconnected pores, shown in a side cross sectional view.

Referring now to FIG. 9A, three alternate embodiments of a fixation implant are shown. Referring to the top image of FIG. 9A, the depicted embodiment is a non-cannulated fixation implant 900 having a head 910 and a distal tip 960 that are not cannulated, and the head 910 including a tool recess 920 for engaging a driving instrument, the implant also having exterior threading 940 and an open scaffold body 950 comprising a scaffold of random open and interconnected pores that is an engineered model based on the porous network of trabecular bone. Referring again to FIG. 9A, in the middle panel is a fixation implant 900' that is a variation of the fixation implant 900 shown above, wherein the shank 930 includes threading 940 along its length and only a portion of the length of the shank 930 is formed of the open scaffold body 950 and a portion of the shank 930 is a through solid 970. Referring to the bottom image of FIG. 9A, the depicted embodiment is a non-cannulated fixation implant 1000 having a head 1010 and a distal tip 1060 that are not cannulated, and the head 1010 including a tool recess 1020 for engaging a driving instrument, the implant also having exterior threading 1040 and a porous body 1050 comprising a framework of random open and interconnected pores that closely mimics the porous network of trabecular bone.

Figure 9B:
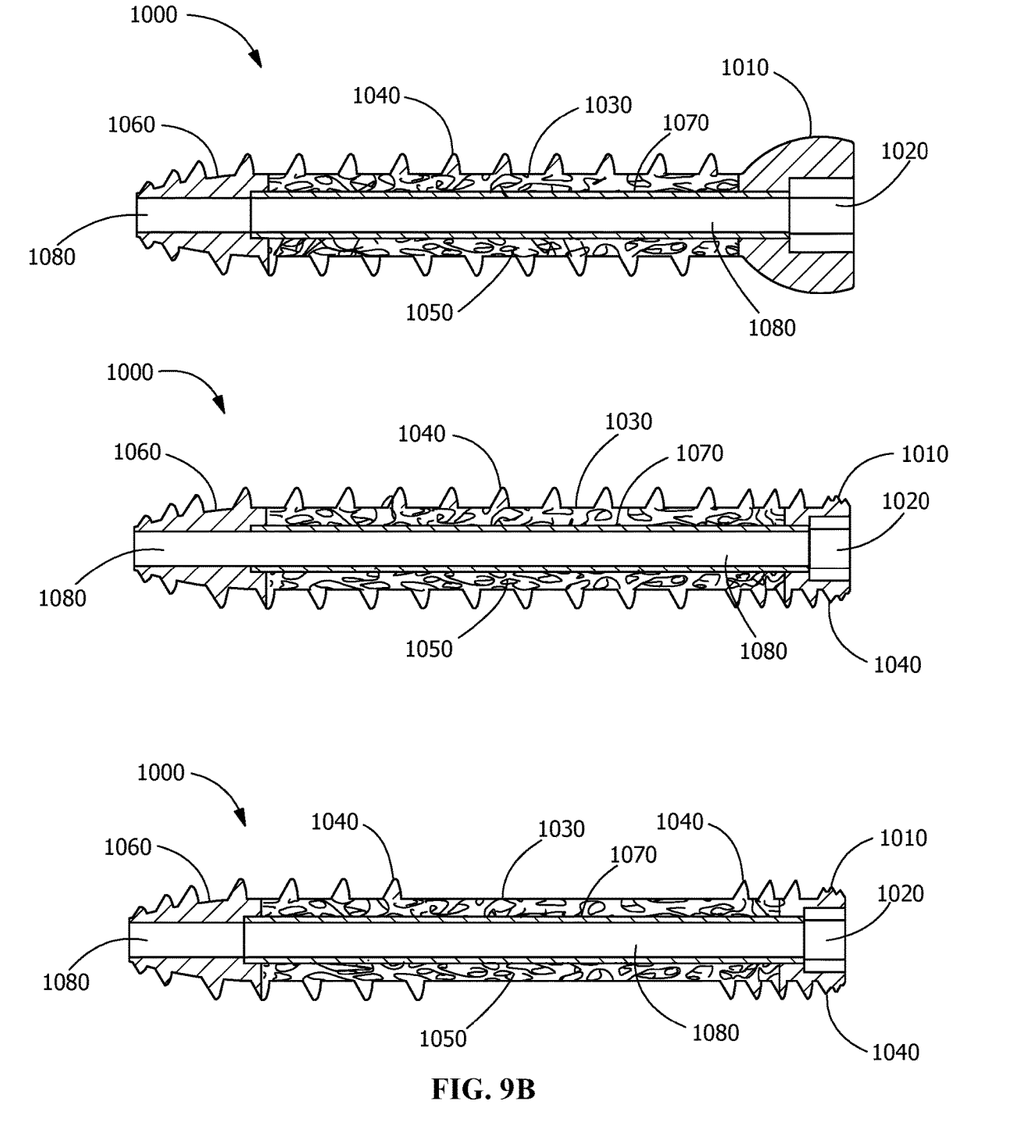

Referring now to FIG. 9B, three alternate embodiments of a fixation implant are shown, each in a side cross sectional view. The uppermost image depicting an cannulated fixation implant 1000 having a solid-walled 1070 inner cylindrical through channel 1080, the implant 100 having exterior threading 1040 and an interior framework of random open and interconnected pores. Referring again to FIG. 9B, the middle image depicts an cannulated implant 1000 having a solid-walled 1070 inner cylindrical through channel 1080, the implant having a cylindrical head 1010, exterior threading 1040 from the head 1010 to the distal tip 1060 and an interior framework of random open and interconnected pores, shown in a side cross sectional view. Referring again to FIG. 9B, the third and bottom image depicts an cannulated implant 1000 having a solid-walled 1070 inner cylindrical through channel 1080, the implant 1000 having a cylindrical head 1010, exterior threading 1040 at the head 1010 and on a portion of the shank 1030 and at the distal tip 1060 and an interior framework of random open and interconnected pores.

In accordance with various embodiments, the open and porous open core of the fixation implant may be formed by any of a variety of processes, including additive (3D) manufacturing, conventional machining, and assembly of subparts. And in some embodiments, the open and porous open core of one or both the head and the shank are formed separately, wherein any threads on the fixation implant are formed from a material selected from metal, and the open core is separately formed using composite material that includes one or more of biocompatible polymers such as PEK, PEEK and PAEK, and other biodegradable polymers, bone material, BMP, and the like.

In some representative embodiments the fixation implant is or resembles a bone screw insofar as such fixation member includes a head and an elongated shank that includes a threaded portion, and in some embodiments, a shank portion that is proximate to the head that is not threaded. It will be appreciated that such fixation members may comprise one or more different thread features that may vary in any one or more number of threads, frequency, pitch, helix angle, thread angle, and major and minor diameters. And the threading may be male (extending away from the fixation implant), female (notches, grooves or channels cut into the fixation implant for receiving male threads), and combinations of these. Further, any one or more of the thread features may be shaped as known in the art, including shapes selected from "V" shaped, square-, buttress-, reverse buttress threaded, and combinations of these, and the thread features may be left or right hand oriented, and the thread features may be self-cutting or self-tapping, or non-self-cutting or non-self-tapping, and combinations of these. Further, the threading may be present only on the shank, or may be present on the shank and one or more of at least a portion of the head and the distal tip. As described variously herein, a fixation member having external threading may alternately be referred to as a screw.

In yet other representative embodiments, the fixation implant is or resembles a bone anchor or plug insofar as such fixation member includes a head and an elongated shank that is only partially threaded. It will be appreciated that in some such embodiments, such fixation members may comprise one or more surface features for enhancing engagement with tissue such as cortical or cancellous bone, such features including but not limited to, keels, fins, and distal bulbs or protuberances. In some embodiments, the fixation implant may have a surface treatment that is suitable for osseo-induction and may be one or more of porous and comprise an osseo-inductive agent, including a biological agent.

In accordance with some embodiments the fixation member has an overall cylindrical, conical, or frusto conical shape that has either a fixed or an increasing diameter from distal to proximal. In some specific embodiments, the head has a frusto conical or a spherical or hemispherical shape. And in some embodiments, the shank has an overall or generally cylindrical shape, with a tapered or conical distal tip. In various embodiments, the fixation member may have a shank that is fully threaded, or it may have a short-unthreaded portion.

As used herein, the term "head" in reference to the proximal head portion of the fixation implant means and includes a structure that is selected from spherical, shaped (e.g., generally spherical with one or more flats), hemi-spherical, frustoconical, discoid, and planar. Thus, in various embodiments with respect to the head, the fixation implant may resemble one of a conventional bone screw, a pedicle screw, a headless screw and other forms, wherein in each instance the head portion of the fixation implant is adapted with at least one feature for facilitating its insertion into bone. In accordance with some embodiments, a fixation member has a head that comprises a flat surface or top and may further comprise an enlarged outer diameter relative to the outer diameter of the shank, wherein the head may include an internal bore with one or more internal engagement features for receiving a driver. Such features may include one or more of a hex configuration for receiving a hex driver, or internal threading for receiving a threaded driver cap, or any of a variety of other possible engagement features. The head and shank of the fixation member, and any threaded driver cap may, in some embodiments, be cannulated for receiving a guide or k-wire there through.

Further still, in some embodiments, the fixation member may be cannulated, in some embodiments only a portion of the fixation member may be cannulated, and in some embodiments the fixation member is not cannulated.

In some such embodiments, the shape of the fixation member may be other than circular in cross section across the elongate axis, and thus the fixation member may have any one of a non-circular shape including ovoid and triangular. In some embodiments, all or only a portion of a fixation member may be circular in cross section and all or other portions of a fixation member may have a cross section that is other than circular, including ovoid and triangular. In some exemplary embodiments, a fixation member may have a frustoconical tip and a proximal adjacent portion that is triangular in cross section such that the tip can be pushed in to a bone hole. Further still, in some embodiments, the fixation member may have the same diameters shared for each of the head, shank and tip.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A fixation implant comprising:
    a shank having a length from a proximal end to a distal end and a solid-walled through cannula formed therethrough, at least a portion of the shank including an open network body selected from the group consisting of a helix, an organized arrangement of trusses, and combinations thereof, the open network body being formed from a metal, a biocompatible polymer, or a combination thereof;

a head that is integral with the shank at its proximal end, the head being formed from a solid material and comprising a tool recess configured for engagement with a driving instrument;

a tip that is integral with the shank at its distal end, the tip being formed from a solid material; and at least one thread formed of solid metal and extending along an external surface of the shank and over the open network body such that the at least one thread is integral with and disposed on an outer surface of the open network body along the entire length of the shank, wherein the open network body is exposed in gaps between the at least one thread.

2. The fixation implant according to claim 1, wherein the head is spherical, partially spherical, or cylindrical.

3. The fixation implant according to claim 1, wherein the biocompatible polymer is selected from the group consisting of PEK, PEEK, PAEK, and combinations thereof.

4. The fixation implant according to claim 1, wherein the solid-walled through cannula is formed through the entirety of the fixation implant from and including the head through the tip.

5. The fixation implant according to claim 4, wherein the solid-walled through cannula comprises one or more fenestrations.

6. The fixation implant according to claim 1, wherein one or more surfaces of the fixation implant comprises a surface treatment that is porous or osseoinductive.

7. The fixation implant according to claim 1, wherein the open network body includes a dual helical body comprising the helix and a secondary helix entwined with the helix, each having a different pitch.

8. A fixation implant comprising:
(i) a shank having a length from a proximal end to a distal end, at least a portion of the shank comprising a ingrowth portion formed from a metal, a biocompatible polymer, or a combination thereof;
(ii) at least one solid metal thread formed on and extending along an external surface of the shank and over the entirety of the ingrowth portion such that the at least one solid metal thread is integral with and disposed on an outer surface of the ingrowth portion;
(iii) a head formed from metal that is non-porous and cylindrical or spherical, the head being integral with the shank at the proximal end of the shank and comprising a tool recess configured for engagement with a driving instrument;
(iv) a threaded tapered tip formed from metal that is non-porous and is integral with the shank at the distal end of the shank; and
(v) a through cannula formed through the head, the shank and the threaded tapered tip, the through cannula being solid-walled through the ingrowth portion of the shank, wherein the ingrowth portion is porous and comprises a helix, an organized arrangement of trusses, or a combination thereof, and is exposed in gaps between the at least one metal thread.

9. The fixation implant according to claim 8, wherein head is cylindrical and threaded.

10. The fixation implant according to claim 9, wherein the threads of the head, the tapered tip, or both the head and the distal tip are different than the at least one metal thread formed on the shank.

11. The fixation implant according to claim 8, wherein the at least one metal thread extends along the entire length of the shank.

12. A fixation implant comprising:
a shank having a length from a proximal end to a distal end and a solid-walled through cannula formed therethrough, a first portion of the shank between the proximal end and a central portion of the shank being solid, and a second portion of the shank between the distal end and the central portion of the shank including an open network body selected from the group consisting of a helix, an organized arrangement of trusses, and combinations thereof, the open network body being formed from a metal, a biocompatible polymer, or a combination thereof;

a head that is integral with the shank at its proximal end, the head being formed from a solid material and comprising a tool recess configured for engagement with a driving instrument;

a tip that is integral with the shank at its distal end, the tip being formed from a solid material; and at least one thread formed of solid metal and extending along an external surface of the shank and over the open network body such that the at least one thread is integral with and disposed on an outer surface of the open network body along the entire length of the shank, wherein the open network body is exposed in gaps between the at least one thread.

13. The fixation implant according to claim 12, wherein the head is spherical, partially spherical, or cylindrical.

14. The fixation implant according to claim 12, wherein the biocompatible polymer is selected from the group consisting of PEK, PEEK, PAEK, and combinations thereof.

15. The fixation implant according to claim 12, wherein the solid-walled through cannula is formed through the entirety of the fixation implant from and including the head through the tip.

16. The fixation implant according to claim 15, wherein the solid-walled through cannula comprises one or more fenestrations.

17. The fixation implant according to claim 12, wherein one or more surfaces of the fixation implant comprises a surface treatment that is porous or osseoinductive.

* * * * *